(12) United States Patent
Kang

(10) Patent No.: US 12,427,026 B2
(45) Date of Patent: *Sep. 30, 2025

(54) METHOD FOR MANUFACTURING BONE GRAFT SUBSTITUTE HAVING HOLES

(71) Applicant: PURGO BIOLOGICS INC., Seongnam-si (KR)

(72) Inventor: Ho Chang Kang, Seongnam-si (KR)

(73) Assignee: PURGO BIOLOGICS INC. (KR)

( * ) Notice: Subject to any disclaimer, the term of this patent is extended or adjusted under 35 U.S.C. 154(b) by 850 days.

This patent is subject to a terminal disclaimer.

(21) Appl. No.: 17/617,304

(22) PCT Filed: Jun. 4, 2020

(86) PCT No.: PCT/KR2020/007297
§ 371 (c)(1),
(2) Date: Dec. 7, 2021

(87) PCT Pub. No.: WO2020/246830
PCT Pub. Date: Dec. 10, 2020

(65) Prior Publication Data
US 2022/0249237 A1    Aug. 11, 2022

(30) Foreign Application Priority Data

Jun. 7, 2019  (KR) .......................... 10-2019-0067391

(51) Int. Cl.
*A61F 2/30* (2006.01)
*A61C 8/00* (2006.01)
(Continued)

(52) U.S. Cl.
CPC ........ *A61F 2/30942* (2013.01); *A61C 8/0006* (2013.01); *A61C 8/0009* (2013.01);
(Continued)

(58) Field of Classification Search
CPC ............... A61L 27/3608; A61L 27/365; A61L 27/3683; A61F 2002/30957; A61F 2002/2835

See application file for complete search history.

(56) References Cited

U.S. PATENT DOCUMENTS 4,138,892 A  *  2/1979  Davis .................... B28B 7/0094
                                                  374/53
6,905,516 B1 *  6/2005  Lemaitre ................... A61F 2/28
                                                  623/23.62
(Continued)

FOREIGN PATENT DOCUMENTS

EP    3415174 A1   12/2018
JP    2003024341 A  1/2003
(Continued)

OTHER PUBLICATIONS

European Extended Search Report for Application No. 20818368.1, mailed Aug. 12, 2022.
(Continued)

*Primary Examiner* — Alison L Hindenlang
*Assistant Examiner* — Alexander A Wang
(74) *Attorney, Agent, or Firm* — Renaissance IP Law Group LLP

(57) ABSTRACT

Provided is a method of manufacturing a bone grafting substitute having a hole. The method of manufacturing a bone grafting substitute having a hole includes a biodegradable polymer preparation operation of preparing biodegradable polymer; a molding material preparation operation of preparing a molding material by mixing the biodegradable polymer with a bone material; a molding material injection operation of injecting the molding material into a hole forming mold for molding a bone grafting substitute having a hole; and a bone grafting substitute having a hole molding (Continued)

operation of drying the molding material injected into the hole forming mold at a predetermined temperature.

25 Claims, 9 Drawing Sheets

(51) Int. Cl.
    *A61C 8/02*     (2006.01)
    *A61F 2/28*     (2006.01)
    *A61L 27/36*     (2006.01)
    *B29C 45/00*     (2006.01)

(52) U.S. Cl.
    CPC ............ *A61F 2/28* (2013.01); *A61L 27/3608* (2013.01); *A61L 27/362* (2013.01); *A61L 27/365* (2013.01); *A61L 27/3683* (2013.01); *B29C 45/00* (2013.01); *A61F 2002/2835* (2013.01); *A61F 2002/30957* (2013.01); *A61L 2430/02* (2013.01); *A61L 2430/12* (2013.01)

(56) References Cited

U.S. PATENT DOCUMENTS

| | | | |
|---|---|---|---|
| 7,381,224 B1* | 6/2008 | Li | ............................ A61L 27/46 623/23.51 |
| 10,034,727 B2 | 7/2018 | Cho et al. | |
| 2002/0029084 A1* | 3/2002 | Paul | .......................... A61F 2/44 623/925 |
| 2003/0039676 A1 | 2/2003 | Boyce et al. | |
| 2006/0216321 A1 | 9/2006 | Lyu et al. | |
| 2009/0312524 A1* | 12/2009 | Lauritzen | ............... A61K 38/17 530/356 |
| 2010/0102479 A1* | 4/2010 | Walls | ..................... B29C 43/36 264/255 |
| 2011/0021753 A1* | 1/2011 | Huang | ................... C07K 14/78 435/68.1 |
| 2017/0000624 A1* | 1/2017 | Schallenberger | ... A61L 27/3608 |
| 2017/0151040 A1* | 6/2017 | Wychowanski | ..... A61C 8/0012 |

FOREIGN PATENT DOCUMENTS

| | | |
|---|---|---|
| KR | 200233742 Y1 | 10/2001 |
| KR | 101661725 B1 | 10/2016 |
| KR | 20170040414 A | 4/2017 |
| KR | 101906899 B1 | 10/2018 |
| KR | 102115806 B1 | 5/2020 |
| WO | 2019231094 A1 | 12/2019 |

OTHER PUBLICATIONS

International Search Report for PCT/KR2020/007297 mailed Sep. 23, 2020.

* cited by examiner

FIG. 1
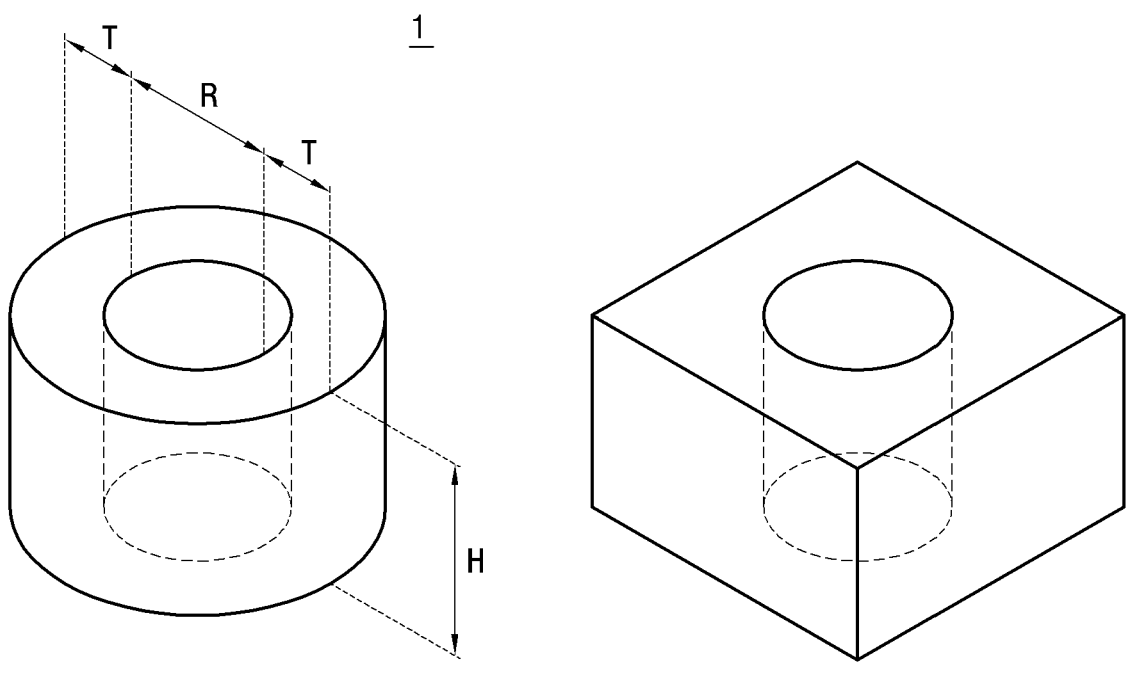
(a)          (b)
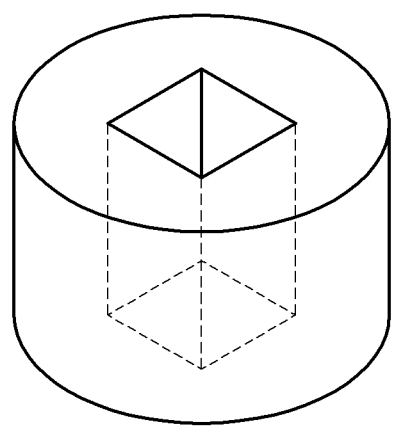
(c)

METHOD FOR MANUFACTURING BONE GRAFT SUBSTITUTE HAVING HOLES

TECHNICAL FIELD

The present inventive concept relates to a method of manufacturing a bone grafting substitute having a hole, and more particularly, to a method of manufacturing a bone grafting substitute having a hole, by which a bone grafting substitute having a hole may be manufactured in high yield by a simple method, so that an implant procedure period is remarkably reduced and sufficient strength to firmly fix an implant is secured.

BACKGROUND ART

Bone grafting substitutes (BGS) are a substitute material used to fill a space in a bone tissue and promote the formation of new bone by replacing a defective part of the bone tissue by degeneration or other tissue loss due to various dental diseases, trauma, diseases, etc.

In detail, during an implant procedure, when the bone quality is poor or the amount of bone is insufficient, or when an alveolar bone is destroyed or lost due to periodontitis, an implant cannot be placed immediately, and thus, a procedure to increase the alveolar bone is necessary. As such, when bone regeneration (osteogenesis) is necessary, guided bone regeneration (GBR) or bone grafting is performed.

When alveolar bone regeneration is completed through guided bone regeneration, an implant is placed through the secondary operation of inserting an implant by incising the gum. In this state, as about 6 months are taken for the completion of regeneration of the alveolar bone and the placement of an implant is achieved through the secondary operation, a long time is taken from the alveolar bone regeneration to the placement of an implant.

To address the above issues, a method of placing a bone grafting substitute in a periodontal tissue tooth extraction recess (cavity in periodontal tissue where tooth is extracted) in an oral cavity, inserting an implant screw therein, and covering the implant screw with a membrane and suturing the same, and then inserting an implant into the screw that is already inserted without the secondary operation, thereby remarkably reducing an implant procedure time, unlike a conventional method of performing the secondary operation of inserting an implant screw by incising gum when alveolar bone regeneration is completed, is required.

Furthermore, a method of manufacturing a bone grafting substitute having a hole, by which a bone grafting substitute having a hole may be manufactured in high yield by a simple method, the bone grafting substitute having a hole being capable of remarkably reducing an implant procedure period and having sufficient strength to firmly fix an implant.

Furthermore, there is a demand for a method of manufacturing a bone grafting substitute in high yield by a simple method, by simultaneously performing the implantation of a bone grafting substitute and the placement of an implant, so that an implant procedure period is remarkably reduced and sufficient strength to firmly fix an implant screw is secured.

DETAILED DESCRIPTION OF THE INVENTIVE CONCEPT

Technical Problem

The present inventive concept provides a method of manufacturing a bone grafting substitute having a hole, the bone grafting substitute having a shape in which a hole is formed, in high yield by a simple method, by simultaneously performing the implantation of a bone grafting substitute and the placement of an implant, so that an implant procedure period is remarkably reduced and sufficient strength to firmly fix an implant screw is secured.

Solution to Problem

According to an aspect of the present inventive concept, a method of manufacturing a bone grafting substitute having a hole includes a biodegradable polymer preparation operation of preparing biodegradable polymer, a molding material preparation operation of preparing a molding material by mixing the biodegradable polymer with a bone material, a molding material injection operation of injecting the molding material into a hole forming mold for molding a bone grafting substitute having a hole, and a bone grafting substitute having a hole molding operation of drying the molding material injected into the hole forming mold at a predetermined temperature.

The method may further include, after the bone grafting substitute having a hole molding operation, a bone grafting substitute having a hole drying operation of drying the bone grafting substitute having a hole, of which molding is completed, by any one selected from among hot air drying and natural drying.

The hole forming mold may include an upper mold provided to mold the bone grafting substitute having a hole and including a plurality of bone grafting substitute main body holes that are formed by penetrating the upper mold and arranged apart from each other, and a lower mold provided, when coupled to the upper mold, to allow the plurality of bone grafting substitute main body holes to form a shape of the bone grafting substitute having a hole, and the molding material injection operation may include combining the upper mold to the lower mold, and injecting the molding material into the hole forming mold in a state in which the upper mold and the lower mold are combined to each other.

The lower mold may include a base, and a plurality of hole forming posts, each of the plurality of hole forming posts protruding upwards from the base, having a cross-sectional area less than a cross-sectional area of each of the plurality of bone grafting substitute main body holes, being arranged at a center area of each of the plurality of bone grafting substitute main body holes, and forming a center hole of the bone grafting substitute having a hole, and in the molding material injection operation, the molding material may be injected into a space formed by the plurality of bone grafting substitute main body holes of the upper mold, the plurality of hole forming posts of the lower mold, and the base.

The base and the plurality of hole forming posts may be integrally provided.

The lower mold may further include a cut portion provided at one side of the base and having a predetermined cut region to facilitate separation of the upper mold from the lower mold in a state in which the upper mold and the lower mold are combined to each other, and when molding by the bone grafting substitute having a hole molding operation is completed, the upper mold and the lower mold may be separated from each other so that the bone grafting substitute having a hole is separated from the hole forming mold.

A coupling post may be provided on the base of the lower mold to be apart from the plurality of hole forming posts, and a location fixing hole may be provided in the upper mold at one side of the plurality of bone grafting substitute main body holes to fix the location of the upper mold on the lower mold through interference fit to the coupling post.

The hole forming mold may include an upper mold in which a plurality of bone grafting substitute main body holes are formed by penetrating the upper mold and arranged apart from each other, to mold the bone grafting substitute having a hole, and a lower mold including a plurality of hole forming posts, each of the plurality of hole forming posts having a cross-sectional area less than a cross-sectional area of each of the plurality of bone grafting substitute main body holes, arranged at a center area of each of the plurality of bone grafting substitute main body holes, and forming a center hole of the bone grafting substitute having a hole, and the upper mold and the lower mold may be integrally provided.

In the bone grafting substitute having a hole drying operation, a temperature for the hot air drying may be 30°-150° C.

The bone grafting substitute having a hole may have any one shape selected from among a circular ring shape and a polygonal block shape.

In the molding material preparation operation, pH of the molding material may be 4.0-9.0.

A particle size of the bone material may be 100 μm-2000 μm.

In the bone grafting substitute having a hole molding operation, molding may be performed by freeze-drying at a temperature lower than room temperature.

The biodegradable polymer may be collagen, the collagen may include porcine ligament-derived collagen, and a collagen preparation operation of preparing the collagen may include a porcine ligament pretreatment operation of pretreating porcine ligament to obtain collagen from the porcine ligament, a collagen dough forming operation of forming the pretreated porcine ligament into collagen dough, a homogenization operation of mixing the collagen dough with an alcohol aqueous solution into a homogenized collagen solution, and a collagen filtering operation of filtering collagen from the homogenized collagen solution.

The porcine ligament pretreatment operation may include removing at least blood vessel and fat from the porcine ligament, dipping the porcine ligament, from which the at least blood vessel and fat are removed, in an alcohol aqueous solution, preparing cured porcine ligament by curing the porcine ligament at a temperature lower than a predetermined reference temperature, and cutting the cured porcine ligament into a predetermined size.

The collagen dough forming operation may include inputting the pretreated porcine ligament into an acid aqueous solution, in which proteolytic enzyme is dissolved, and mixing a mixture using a Stephan mixer, preparing a first mixture by adding an acid aqueous solution to a mixed solution and agitating a mixture, preparing a first dough by removing liquid from the first mixture obtained through agitation, preparing a second mixture by inputting the first dough into a basic solution and agitating a mixture, and adjusting pH, preparing a second dough by removing liquid from the second mixture obtained through agitation, preparing a third mixture by inputting the second dough into an alcohol aqueous solution and agitating a mixture, and forming collagen dough by removing liquid from the third mixture obtained through agitation.

The biodegradable polymer may be collagen, the collagen may include porcine skin-derived collagen, and a collagen preparation operation may include a porcine skin pretreatment operation of pretreating porcine skin to obtain collagen from the porcine skin, a collagen dough forming operation of forming the pretreated porcine skin into collagen dough, a homogenization operation of mixing the pretreated porcine skin with an alcohol aqueous solution into a homogenized collagen solution, and a collagen filtering operation of filtering collagen from the homogenized collagen solution.

The porcine skin pretreatment operation may include cutting frozen porcine skin into a predetermined size, removing fat by inputting cut porcine skin into an organic solvent and agitating a mixture, and removing the organic solvent by washing out porcine skin, from which fat is removed, with distilled water.

The collagen filtering operation may include centrifuging the homogenized collagen solution, and obtaining collagen by removing supernatant liquid generated after centrifugation.

The collagen may include cross-linked collagen that is cross-linked to have a cross-linked structure, The method may further include, after the collagen filtering operation, a fibrillation buffer mixing operation of preparing a mixed solution by mixing the collagen obtained in the collagen filtering operation with a fibrillation buffer having 20-30 parts by weight of sodium chloride, 1-3 parts by weight of sodium hydroxide, and 3-5 parts by weight of di-sodium hydrogen phosphate dihydrate with respect to 100 parts by weight of water, a gel state change operation of preparing a gel state mixture by mixing the mixed solution with γ-PGA and inputting a mixture into a well plate to change the mixture to be in a gel state in an incubator, a crosslinking reaction processing operation of forming cross-linked collagen by mixing the gel-state mixture with a cross linking solution to have a crosslinking reaction, a washing operation of washing out the cross linking solution mixed in the crosslinking reaction processing operation, a homogenization operation after crosslinking processing of dissolving the cross-linked collagen in a solvent to produce a homogenized cross-linked collagen solution, and a cross-linked collagen filtering operation of filtering the cross-linked collagen from the homogenized cross-linked collagen solution.

The washing operation may include preparing a first mixture by tearing the cross-linked collagen into small pieces and inputting the pieces into an alcohol aqueous solution, preparing a filtrate by agitating the first mixture and decompression-filtering a mixture, preparing a second mixture by tearing the filtrate into small pieces and inputting the pieces into an alcohol aqueous solution, and agitating the second mixture and decompression-filtering a mixture.

The biodegradable polymer may include any one biodegradable polymer selected from among fibrinogen, chitosan, gelatin, cellulose, hyaluronic acid, dextran, and cross-linked fibrinogen, cross-linked chitosan, cross-linked gelatin, cross-linked cellulose, cross-linked hyaluronic acid, and cross-linked dextran, which are cross-linked to have a cross-linked structure.

The bone material may include any one heterogeneous bone selected from among bovine bones, horse bones, and porcine bones.

The bone material may include any one selected from among artificially synthesized bone such as bioceramic-based bone containing calcium phosphate and natural ceramic such as coral.

In the bone grafting substitute having a hole, a thickness of a bone grafting substitute main body surrounding the hole may be 1.5 mm-5 mm.

The bone grafting substitute having a hole may have a hole having a diameter of 2 mm-8 mm and a height of 2 mm-10 mm.

Advantageous Effects

According to an embodiment of the present inventive concept, a bone grafting substitute having a hole may be manufactured in high yield by a simple method, by using a hole forming mold to form a bone grafting substitute having a hole, which may remarkably reduce an implant procedure period because the secondary surgical operation for the placement of an implant is unnecessary by simultaneously performing the implantation of a bone grafting substitute and the placement of an implant.

DESCRIPTION OF THE DRAWINGS

FIG. 1 is a perspective view showing various shapes of a bone grafting substitute having a hole manufactured according to an embodiment of the present inventive concept.

MODE OF THE INVENTIVE CONCEPT

Figure 2:
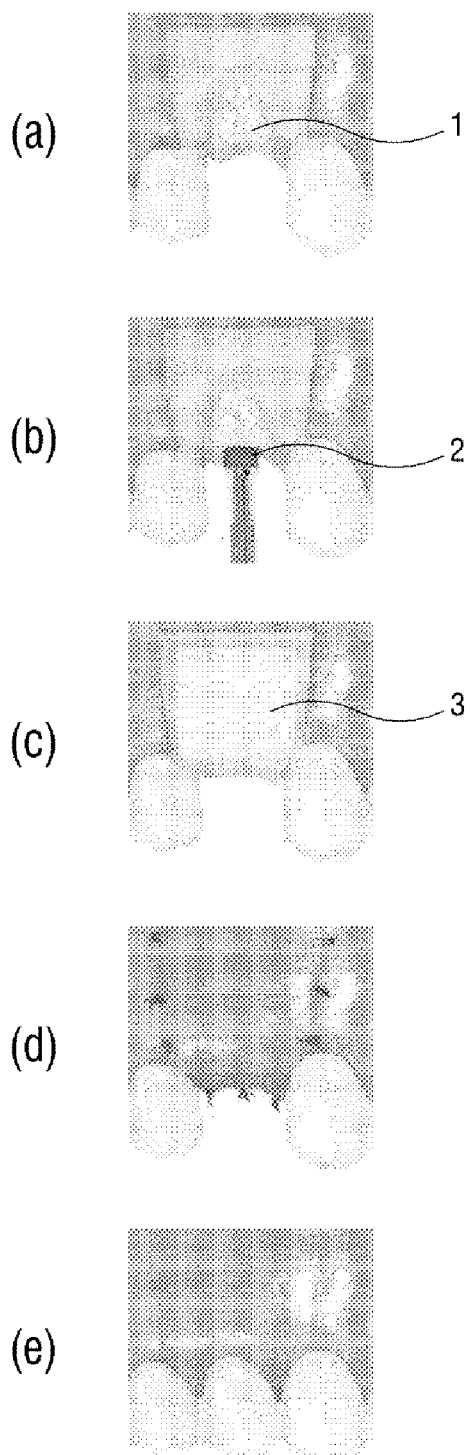
FIG. 2 is a view illustrating a bone grafting operation process using a bone grafting substitute having a hole according to an embodiment of the present inventive concept.

In order to fully understand the operational advantages of the present inventive concept and the objectives achieved by the implementation of the present inventive concept, the accompanying drawings illustrating preferred embodiments of the present inventive concept and the contents described in the accompanying drawings are referred to.

Hereinafter, the inventive concept will be described in detail by explaining preferred embodiments of the inventive concept with reference to the attached drawings. Like reference numerals in the drawings denote like elements.

FIG. 1 is a perspective view showing various shapes of a bone grafting substitute having a hole manufactured according to an embodiment of the present inventive concept. FIG. 2 is a view illustrating a bone grafting operation process using a bone grafting substitute having a hole according to an embodiment of the present inventive concept.

As illustrated in these drawings, a bone grafting substitute (a) having a hole according to an embodiment of the present inventive concept has a ring shape having a hole having a diameter R at the center, a thickness T of a bone grafting substitute main body surrounding the hole, and a height H.

As another shape, although a bone grafting substitute (b) having a hole has a circular hole in the center like the bone grafting substitute (a), the bone grafting substitute (b) is different from the bone grafting substitute (a) in that the former has an overall rectangular block shape.

As another shape, although a bone grafting substitute (c) having a hole formed at the center has an overall circular ring shape like the bone grafting substitute (a), the bone grafting substitute (c) is different from the bone grafting substitute (a) in that the former has a hole having a rectangular cross-section formed at the center.

The bone grafting substitutes having a hole of FIG. 1 are merely examples of bone grafting substitutes having a hole according to the present inventive concept, and the present inventive concept is not limited thereto. According to the placement position of a bone grafting substitute and the like, the overall shape of the bone grafting substitute may be formed in various shapes including not only a circular ring or a rectangle block, but also a polygonal block and the like. According to the shape of an implant inserted in the hole formed in the bone grafting substitute, and the like, the hole formed at the center of the bone grafting substitute may be formed in various shapes such as circular, polygonal, and the like.

As the bone grafting substitute is formed in a shape in which the hole is formed, the bone grafting substitute having a hole is placed in periodontal tissue tooth extraction recess (cavity in periodontal tissue where tooth is extracted) in the oral cavity, and an implant screw is inserted through a center hole of the bone grafting substitute having a hole and then covering the site with a membrane and suturing the same. Accordingly, unlike the conventional method of performing the secondary operation of inserting an implant by incising gum after alveolar bone regeneration is completed, as an implant is inserted into the screw that is already inserted, without the secondary operation, a time for an implant procedure may be remarkably reduced.

To describe the above in detail with reference to FIG. 2, in operation (a), a bone grafting substitute 1 having a hole manufactured according to an embodiment of the present inventive concept is inserted into a recess portion where an alveolar bone is broken after a tooth is extracted; in operation (b), an implant screw 2 is fixedly inserted into a center hole of the bone grafting substitute having a hole; in operation (c), an operation site is covered with a membrane 3; in operation (d), a procedure is completed by suturing gum; in operation (e), after alveolar bone regeneration is completed, an implant is inserted into a screw portion, thereby completing a treatment.

Accordingly, when bone grafting operation is performed by using the bone grafting substitute having a hole, the implantation of a bone grafting substitute and the placement of an implant screw may be simultaneously performed, and thus an implant procedure period may be remarkably reduced without the secondary surgical operation for the placement of an implant screw.

In this state, in the bone grafting substitute 1 having a hole, the thickness T of the bone grafting substitute main body surrounding the hole may be 1.5 mm to 5 mm. When the thickness is less than 1.5 mm, the shape of the hole may not be retained, and bone having an appropriate thickness is not generated around the implant so that the implant may not be placed.

Furthermore, when the thickness is 5 mm or more, the size of a grafting substitute becomes excessively large so that use inconvenience may be caused.

Accordingly, in the bone grafting substitute 1 having a hole, the thickness T of the bone grafting substitute main body surrounding the hole is formed according to the shape and depth of a tooth extraction recess, according to the present embodiment, the thickness T of a ring shape is 2 mm-4 mm.

The diameter R of the hole at the center of the bone grafting substitute 1 having a hole may be 2 mm to 8 mm. When the diameter is less than 2 mm, an implant may not be inserted, and as an implant having a diameter of 8 mm or more is difficult to exist and practically impossible to use.

Accordingly, the diameter R of the hole of the bone grafting substitute 1 having a hole may be adjusted by using a dental cutting instrument according to the thickness of an implant in use. According to the present embodiment, the diameter R of the hole at the center may be 2 mm-8 mm.

The height of the bone grafting substitute 1 having a hole may be adjusted according to the shape and depth of the tooth extraction recess. According to the present embodiment, the height of the bone grafting substitute 1 having a hole may be 2 mm-10 mm.

Figure 3:
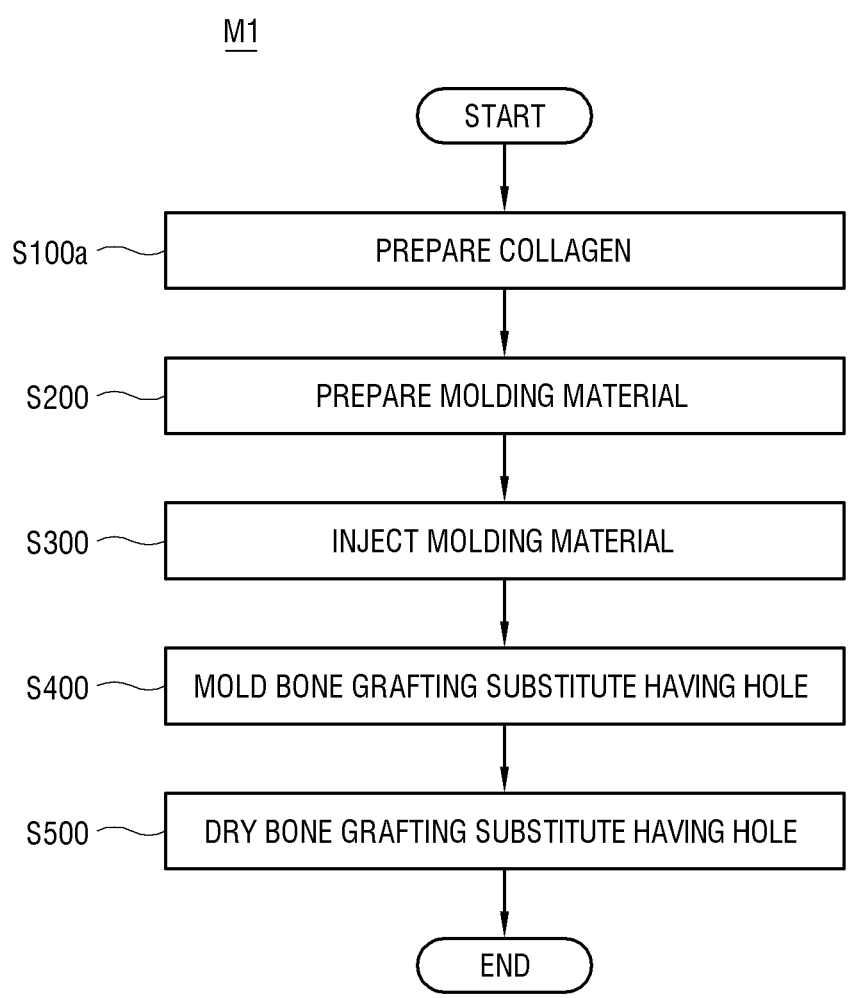
FIG. 3 is a flowchart showing, step by step, a method of manufacturing a bone grafting substitute having a hole according to a first embodiment of the present inventive concept.
Figure 4:
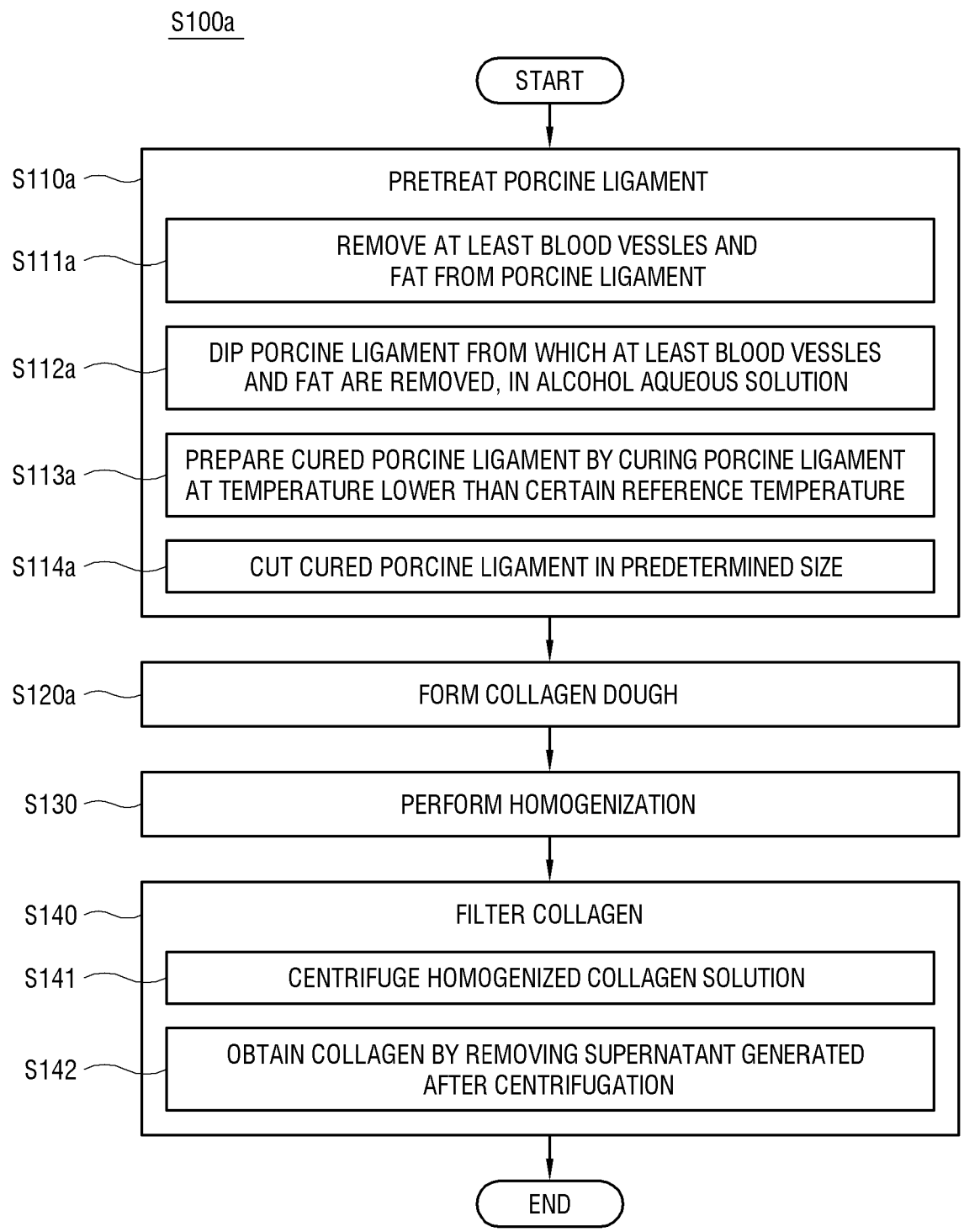
FIG. 4 is a flowchart showing, step by step, a collagen preparing operation of preparing porcine ligament-derived collagen, according to a first embodiment of the present inventive concept.
Figure 5:
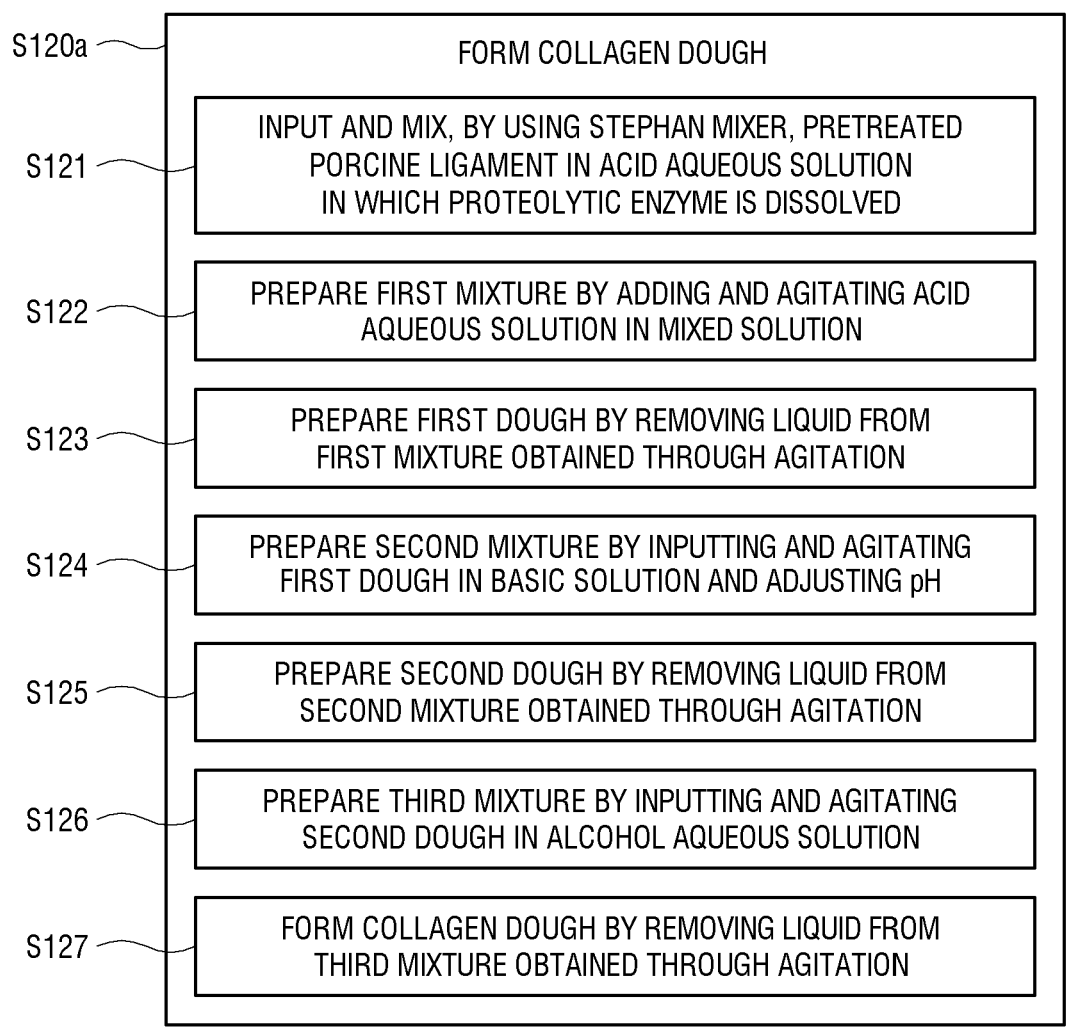
FIG. 5 is a flowchart showing, step by step, a collagen dough forming operation of FIG. 4.
Figure 6:
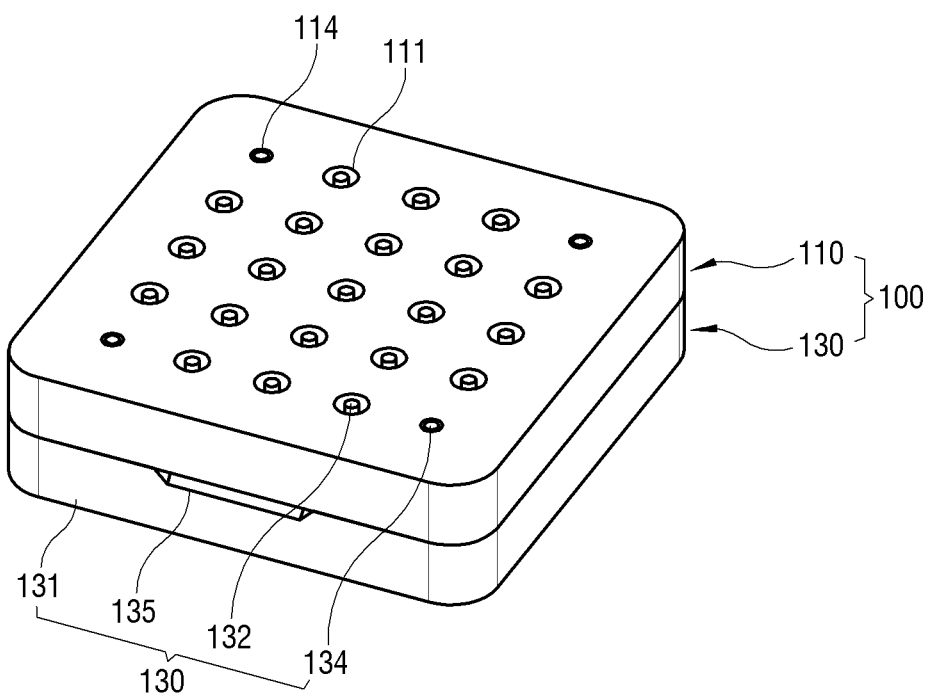
FIG. 6 is a perspective view showing a state in which an upper mold and a lower mold of a hole forming mold are combined with each other.
Figure 7:
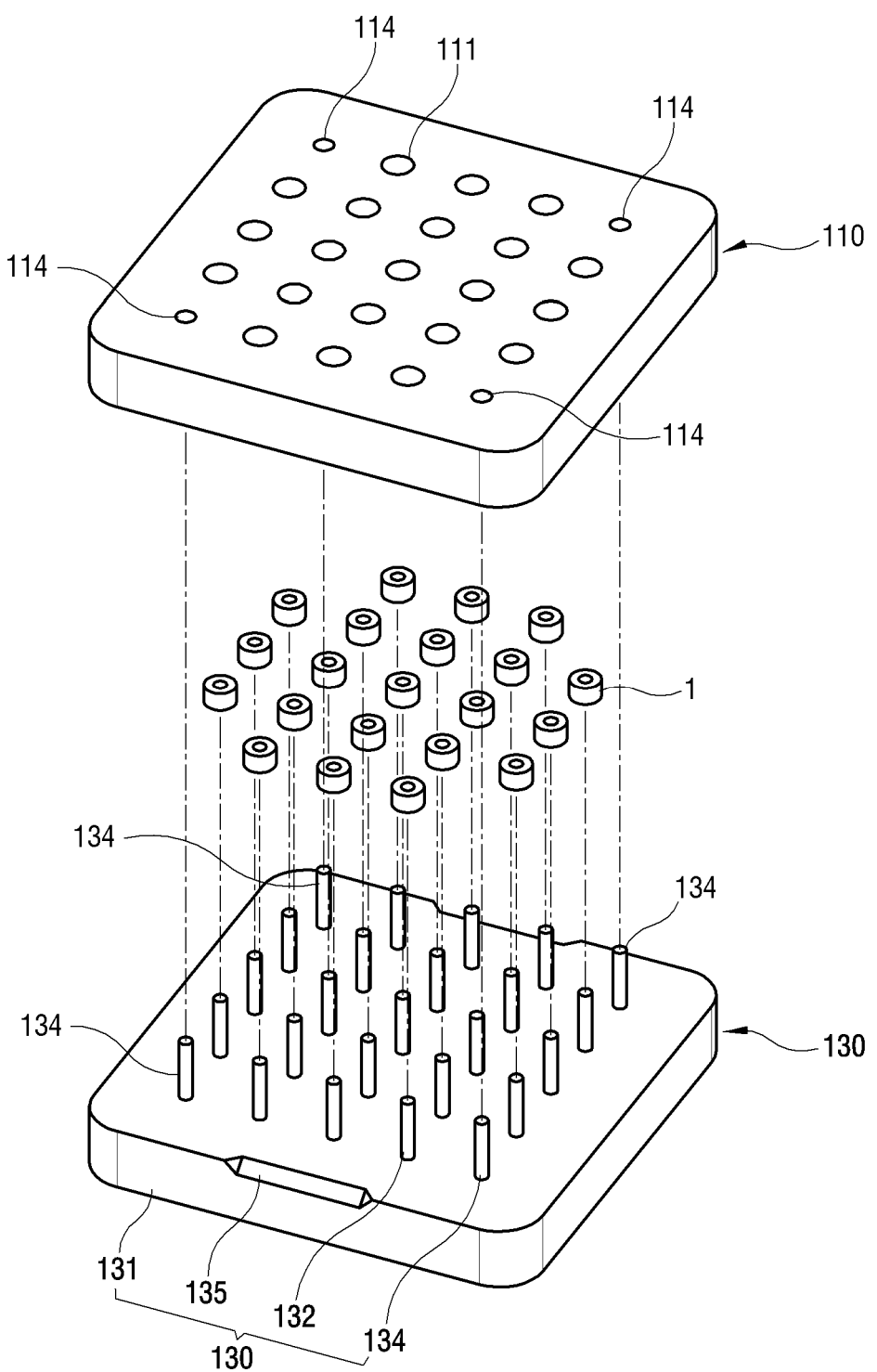
FIG. 7 is a perspective view showing a state in which the upper mold and the lower mold of the hole forming mold are separated from each other.

FIG. 3 is a flowchart showing, step by step, a method of manufacturing a bone grafting substitute having a hole according to a first embodiment of the present inventive concept. FIG. 4 is a flowchart showing, step by step, a collagen preparing operation of preparing porcine ligament-derived collagen, according to a first embodiment of the present inventive concept. FIG. 5 is a flowchart showing, step by step, a collagen dough forming operation of FIG. 4. FIG. 6 is a perspective view showing a state in which an upper mold and a lower mold of a hole forming mold are combined with each other. FIG. 7 is a perspective view showing a state in which the upper mold and the lower mold of the hole forming mold are separated from each other.

As illustrated in these drawings, a method M1 of manufacturing a bone grafting substitute having a hole according to a first embodiment of the present inventive concept may include a collagen preparation operation S100a, a molding material preparation operation S200, a molding material injection operation S300, a bone grafting substitute having a hole molding operation S400, and a bone grafting substitute having a hole drying operation S500.

First, the collagen preparation operation S100a is an operation for preparing collagen to be mixed as a molding material with a bone material that is described below.

The collagen is one of biodegradable polymers, and collagen, fibrinogen, chitosan, gelatin, cellulose, hyaluronic acid, dextran, and the like, and cross-linked collagen, cross-linked fibrinogen, cross-linked chitosan, cross-linked gelatin, cross-linked cellulose, cross-linked hyaluronic acid, cross-linked dextran, and the like, which are obtained by cross-linking the above materials to have a cross-linked structure, can be used as the biodegradable polymer.

Although in the embodiments of the present inventive concept, a case of using collagen is mainly described, not only collagen, but also the above-examples other biodegradable polymers may be used, and the disclosure is not limited thereto.

Collagen is a structural protein that composes tissues and organs of the human body, is the main component of connective tissue, and refers to an animal fibrous protein composed of about 18 amino acids including glycine, proline, and the like. In the case of humans, the collagen is a special structural protein that accounts for 35% that is the most of 5,000 types of proteins that make up the human body.

In particular, collagen is abundant in skin, bones, and tendons, in a shape in which various amino acids are combined in the form of a polypeptide and twisted into three strands, and has a very large molecular weight of about 300,000.

There are several types of collagen by kinds, regions, and types of animals, and each collagen has different characteristics as well as different biomolecules or different components of protein compositions and the like. Accordingly, using necessary human compatible collagen is preferable.

As such collagen, animal-derived collagen, preferably bovine- or porcine-derived collagen, may be used.

Porcine-derived collagen refers to collagen extracted from tissue of the epidermis and the like of pigs. Pigs are safe from concerns of mad cow disease and the like, and have gene sequence similar to that of humans, and thus are used as various substitute materials. Among the porcine-derived collagens, when collagen particularly derived from porcine ligament is used, mechanical properties such as tensile strength and of the like may be excellent.

The porcine-derived collagen may be manufactured from skin, tendon, tail, and the like of pigs, and is composed of type 1 and 3 collagen having no odor and color and having a structure similar to that of the human body.

Furthermore, porcine-derived collagen is safe from pathogenic sources of other animals (mad cow disease EBS and the like), human cadavers (AIDS virus), and the like. The porcine-derived collagen has a pH of 7.0, a molecular weight of about 2000, and excellent tensile strength and elongation compared to existing materials. Furthermore, the total protein content of porcine-derived collagen is 99.9% purity, and the porcine-derived collagen has a viscosity is 25 mps or more and a specific gravity of 0.35-0.39.

Such porcine-derived collagen may include porcine ligament-derived collagen, porcine skin-derived collagen, and cross-linked collagen cross-linked to have a cross-linked structure. According to the first embodiment of the present inventive concept, porcine ligament-derived collagen may be prepared by using a method of preparing porcine ligament-derived collagen, and methods of preparing porcine skin-derived collagen and cross-linked collagen are described below in other embodiments.

First, the collagen preparation operation S100a of preparing porcine ligament-derived collagen may include, as illustrated in detail in FIGS. 4 and 5, a porcine ligament pretreatment operation S110a, a collagen dough forming operation S120a, a homogenization operation S130, and a collagen filtering operation S140.

The porcine ligament pretreatment operation S110a is an operation of pretreating porcine ligament to obtain collagen from the porcine ligament, and may include removing at least blood vessel and fat from the porcine ligament (S111a), dipping porcine ligament, from which at least blood vessel and fat are removed, in an alcohol aqueous solution (S112a), preparing cured porcine ligament by curing a solution in which the porcine ligament is mixed at a temperature lower than a certain reference temperature (S113a), and cutting the cured porcine ligament in a predetermined size (S114a).

The alcohol used in the dipping of the porcine ligament, from which at least blood vessel and fat are removed, in the alcohol aqueous solution (S112a) may include methanol, ethanol, propanol, and isopropanol, and in the alcohol aqueous solution, a mixture ratio of water and alcohol is 50%-90%, preferably 60-80%. When the amount of alcohol is 50% or less, it may be difficult to remove virus in the porcine ligament, and when 90% or more, it may be difficult to cure.

The collagen dough forming operation S120a is an operation of forming the pretreated porcine ligament into collagen dough, and may include inputting and mixing pretreated porcine ligament in an acid aqueous solution, in which proteolytic enzyme is dissolved (S121), preparing a first mixture by adding an acid aqueous solution to a mixed solution and then agitating the mixture (S122), preparing a first dough by removing liquid from the first mixture obtained through agitation (S123), preparing a second mixture by inputting the first dough into a basic solution and agitating the mixture, and then adjusting pH (S124), preparing a second dough by removing liquid from the second mixture obtained through agitation (S125), preparing a third mixture by inputting the second dough into an alcohol aqueous solution and agitating the mixture (S126), and forming collagen dough by removing liquid from the third mixture obtained through agitation (S127).

Examples of the proteolytic enzyme used in the inputting and mixing of the pretreated porcine ligament in the acid aqueous solution, in which proteolytic enzyme is dissolved (S121) may include pepsin, bromelain, chymopapain, chymotrypsin, collagenase, ficin, papain, peptidase, proteolytic enzyme A, proteolytic enzyme K, trypsin, proteolytic enzyme of a microorganism, and a mixture thereof, but the disclosure is not limited thereto.

Although strong acid such as hydrochloric acid and weak acid such as acetic acid may be used as the acid solution used in the operation, preferably weak acid is used, and a mixing ratio of water and acid is 1%-20%, preferably 3%-10%. When the amount of acid is small, removing telopeptide is not smoothly performed, and when the amount is too much, not only telopeptide is removed, but also collagen is damaged.

In the preparing of the second mixture by inputting the first dough into the basic solution and agitating the mixture, and then adjusting pH (S124), pH is 6-8 and may be adjusted by neutralizing with a weak base such as $Na_2CO_3$, $NaHCO_3$, $Na_2HPO_4$, and $NaH_2PO_4$.

In the preparing of the third mixture by inputting the second dough into the alcohol aqueous solution and agitating the mixture (S126), the alcohol may be methanol, ethanol, propanol, and isopropanol, and as solubility of collagen is affected by a mixing ratio of water and alcohol, the mixing ratio of water and alcohol is 5%-40%, preferably 10%-35%.

The homogenization operation S130 is an operation of mixing the collagen dough with the alcohol aqueous solution into a homogenized collagen solution, in which the collagen dough obtained from the collagen dough forming operation S120a is agitated with the alcohol aqueous solution and homogenized by using a homogenizer, thereby obtaining a homogenized collagen solution.

In this state, the alcohol may be methanol, ethanol, propanol, and isopropanol, as the solubility of collagen is affected by the mixing ratio of water and alcohol, the mixing ratio of water and alcohol is 5%-40%, preferably 10%-35%.

The collagen filtering operation S140 is an operation of filtering collagen from the homogenized collagen solution, and may include centrifuging the homogenized collagen solution (S141) and obtaining collagen by removing supernatant liquid generated after centrifugation (S142).

The molding material preparation operation S200 is an operation of preparing a molding material by mixing collagen with a bone material.

In this state, the bone material may be any one heterogeneous bone selected from among bovine bones, horse bones, and porcine bones, and any one selected from artificially synthesized bone such as bioceramic-based bone containing calcium phosphate and natural ceramic such as coral be used therefor. The particle size of the bone material may have a size selected from a range of 100 μm-2000 μm.

The collagen passing through the collagen filtering operation S140 is sediment obtained by using a centrifugation method and in a dough state, and a molding material may be prepared by inputting the collagen into the alcohol aqueous solution and agitating the mixture, and then mixing the bone material. In this state, the alcohol in use may include methanol, ethanol, propanol, and isopropanol, and the mixing ratio of water and alcohol is 5%-40%, preferably 10%-35%.

In the present embodiment, pH of the molding material prepared through the molding material preparation operation S200 may be adjusted within a range of 4.0-9.0.

The molding material injection operation S300 is an operation of injecting the molding material into a hole forming mold for molding a bone grafting substitute having a hole, and the bone grafting substitute having a hole molding operation S400 is an operation of molding a bone grafting substitute having a hole by drying the molding material injected into the hole forming mold at a predetermined temperature.

In this state, in the bone grafting substitute having a hole molding operation, the bone grafting substitute having a hole may be molded by freeze-drying the molding material at a temperature lower than the room temperature.

The structure of a hole forming mold 100 is described below in detail with reference to FIGS. 6 and 7.

The hole forming mold 100 is where the molding material for molding the bone grafting substitute 1 having a hole is injected, in which the injected molding material is molded in a bone grafting substitute having a hole by drying the injected molding material at a predetermined temperature, and the hole forming mold 100 may include an upper mold 110 and a lower mold 130.

First, the upper mold 110 is provided with a plurality of bone grafting substitute main body holes 111 formed by penetrating the upper mold 110 and arranged apart from each other, to mold the bone grafting substitute 1 having a hole. The bone grafting substitute main body holes 111 form the exterior of the bone grafting substitute 1 having a hole.

In the upper mold 110, a location fixing hole 114 for fixing the location of the upper mold 110 on the lower mold 130 through interference fit to a coupling post 135 that is described below is formed at one side of the bone grafting substitute main body holes 111.

In the present embodiment, as illustrated in detail in FIGS. 6 and 7, the bone grafting substitute main body holes 111 are arranged in the form of a rectangle and the location fixing hole 114 is arranged at each corner of the rectangle, but the present inventive concept is not limited thereto, and the bone grafting substitute main body holes 111 and the location fixing hole 114 may be arranged in various numbers and shapes, for example, the numbers of the bone grafting substitute main body holes 111 and the location fixing hole 114 may be increased or decreased according to the size and shape of the hole forming mold 100.

In the meantime, when the lower mold 130 is coupled to the upper mold 110, the bone grafting substitute main body holes 111 may serve to form the shape of the bone grafting substitute 1 having a hole, and the lower mold 130 may include a base 131, a plurality of hole forming posts 132, the coupling post 134, and a cut portion 135.

The base 131 supports the molding material and forms a lower portion of the bone grafting substitute 1 having a hole.

The hole forming posts 132 are each provided to protrude upwards from the base 131 and have a cross-sectional area less than a cross-sectional area of each of the bone grafting substitute main body holes 111, and are each arranged at a center area of the bone grafting substitute main body holes 111 to form the center hole of the bone grafting substitute 1 having a hole.

In the present embodiment, although the base 131 and the hole forming posts 132 are integrally provided, the present inventive concept is not limited thereto, and the base 131 and the hole forming posts 132 may be manufactured in the form of an assembly so that the hole forming posts 132 that are separately manufactured in various shapes are exchangeably coupled to each other according to a desired shape of a hole.

The coupling post 134 is provided on the base 131 of the lower mold 130 apart from the hole forming posts 132, and is coupled, by interference fit, to the above-described location fixing hole 114 of the upper mold 110, thereby fixing the location of the upper mold 110 on the lower mold 130.

The cut portion 135 is provided at one side of the base 131 to allow the upper mold 110 and the lower mold 130 to be separated from each other from a coupled state. The cut portion 135 is provided by cutting a predetermined region.

In the following description, the molding material injection operation S300 and the bone grafting substitute having a hole molding operation S400, which are performed by using the hole forming mold 100 having the above structure, are described.

First, the molding material injection operation S300 is performed, as illustrated in FIG. 6, in a state in which the upper mold 110 and the lower mold 130 of the hole forming mold 100 are combined with each other. The injected molding material fills a space formed by the bone grafting substitute main body holes 111 of the upper mold 110, the hole forming posts 132 of the lower mold 130, and the base 131 of the lower mold 130.

In this state, as the coupling post 134 of the lower mold 130 is coupled, by interference fit, to the location fixing hole 114 of the upper mold 110 to fix the location of the upper mold 110 on the lower mold 130, the space into which the molding material is injected may be prevented from being deformed.

Then, when molding by the bone grafting substitute having a hole molding operation S400 is completed, as illustrated in FIG. 7, the upper mold 110 and the lower mold 130 are separated from each other by a simple operation so that each formed bone grafting substitute 1 having a hole may be simply separated from the hole forming mold 100.

As such, by forming the bone grafting substitute 1 having a hole using the hole forming mold 100 having a simple structure capable of combining the upper mold 110 and the lower mold 130 to each other and separating the same from each other, the bone grafting substitute 1 having a hole may be manufactured by a simple method in high yield.

In the present embodiment, as the hole forming mold 100 has a structure capable of combining and separating the upper mold 110 and the lower mold 130 with respect to each other, an excellent effect of simply separating the bone grafting substitute 1 having a hole from the hole forming mold 100 is obtained. However, the present inventive concept is not limited thereto, and a structure in which the upper mold 110 and the lower mold 130 are integrally provided may be possible.

The bone grafting substitute having a hole drying operation S500 is an operation of drying a bone grafting substitute having a hole, which is completely formed, by any one selected from among hot air drying or natural drying. Although in the present embodiment, natural drying is performed, but the present inventive concept is not limited thereto, and the temperature and the time may vary according to drying conditions.

For hot air drying, the bone grafting substitute having a hole drying operation S500 may be performed at a temperature range of 30° C.-150° C.

In the following description, a process of manufacturing a bone grafting substitute having a hole by a method of manufacturing a bone grafting substitute having a hole according to a first embodiment of the present inventive concept including the above operations is described.

In a description based on porcine ligament of 1 kg, first, blood vessel, fat, and the like are removed through trimming, and the trimmed porcine ligament is dipped in a 60% IPA aqueous solution 10 kg, washed out with purified water 10 kg, and cured at low temperature, and then the cured ligament is cut through a slicer, thereby completing pretreatment of a porcine ligament.

Next, the cut ligament and a 5% acetic acid aqueous solution of 6 kg, in which ficin of 10 g is dissolved, are input and agitated, and then a 10% acetic acid aqueous solution of 8 kg is input therein and agitated for 6 minutes and filtered.

The obtained dough is input into an aqueous solution obtained by dissolving Na2HPO4 of 107 g in purified water 7 kg and agitated, and after filtering the solution, an IPA aqueous solution 7 kg is input therein and agitated to adjust the pH of the solution to be 6, and then the solution is filtered and formed into collagen dough. Next, a 20% IPA aqueous solution of 11 kg is input and agitated, and then the solution is homogenized by a homogenizer.

Next, the solution is centrifuged and supernatant liquid is discarded to obtain collagen. A 20% isopropyl alcohol (IPA) aqueous solution 7 kg is input into the collagen and agitated by a homogenizer, and then a bone material of 130 g is mixed therewith, thereby preparing a molding material.

Next, by pouring the molding material into the hole forming mold and freeze-drying the same, the bone grafting substitute can be formed into a hole-formed shape.

Next, by naturally drying the freeze-dried bone grafting substitute having a hole, the manufacturing process of the bone grafting substitute having a hole is completed.

As such, according to the present embodiment, the bone grafting substitute having a hole may be manufactured more easily. Furthermore, as the implantation of a bone grafting substitute and the placement of an implant may be simultaneously performed, the secondary surgical operation for the placement of an implant is unnecessary, and thus an implant procedure period may be remarkably reduced.

Furthermore, by mixing the collagen and the bone material to form a bone grafting substitute having a hole, it is possible to manufacture the bone grafting substitute having a hole that can have sufficient strength to firmly fix an implant.

Figure 8:
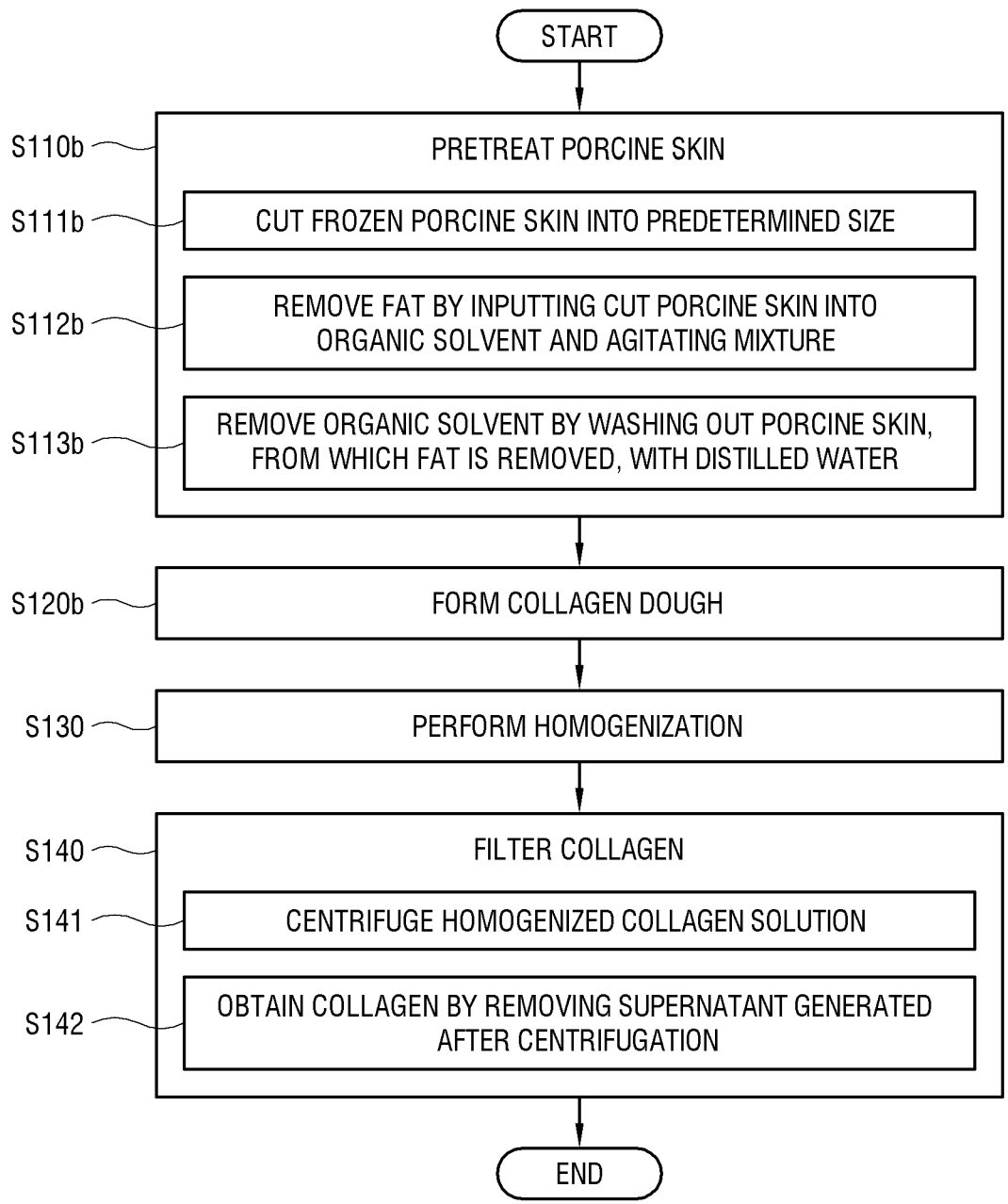
FIG. 8 is a flowchart showing, step by step, a collagen preparing operation of preparing porcine skin-derived collagen, according to a first embodiment of the present inventive concept.

FIG. 8 is a flowchart showing, step by step, a collagen preparing operation of preparing porcine skin-derived collagen, according to a first embodiment of the present inventive concept.

According to a method of manufacturing a bone grafting substitute having a hole according to a second embodiment of the present inventive concept, compared with the first embodiment, there is a difference in preparing porcine skin-derived collagen instead of porcine ligament-derived collagen in a collagen preparation operation S100b. However, there is not much difference in the other operations of manufacturing a bone grafting substitute having a hole therebetween, the collagen preparation operation S100b is mainly described.

The collagen preparation operation S100b of preparing porcine skin-derived collagen may include, as illustrated in detail in FIG. 8, a porcine skin pretreatment operation S110b, a collagen dough forming operation S120b, the homogenization operation S130, and the collagen filtering operation S140.

The porcine skin pretreatment operation S110b, which is an operation of pretreating porcine skin to obtain collagen from porcine skin, may include cutting frozen porcine skin into a preset size (S111b), removing fat by inputting cut porcine skin into an organic solvent and agitating the mixture (S112b), and removing the organic solvent by washing out porcine skin, from which fat is removed, with distilled water (S113b).

The organic solvent is any one selected from among acetone, ethyl acetate, and chloroform, and instead of the organic solvent, any one alcohol selected from among methanol, ethanol, and isopropanol may be used.

In the present embodiment, acetone was used as the organic solvent acetone, the frozen porcine skin was cut into a constant size, and then the cut skin pieces were input into the acetone, agitated twice for 2 hours to remove fat, and washed out 5 times with distilled water, thereby removing the acetone.

The collagen dough forming operation S120b of forming collagen dough using the pretreated porcine skin is similarly performed to the collagen dough forming operation S120a of the first embodiment.

The collagen dough forming operation S120b may include inputting the pretreated porcine skin into an acid solution, in which proteolytic enzyme is dissolved, and mixing the same, preparing a first mixture by adding an acid solution to the mixed solution and agitating the mixture, preparing a first dough by filtering the first mixture obtained through agitation, preparing a second mixture by inputting the first dough into a basic solution and agitating the mixture, and then adjusting pH, preparing a second dough by filtering the second mixture obtained through agitation, preparing a third mixture by inputting the second dough into an alcohol aqueous solution and agitating the mixture, and forming collagen dough by filtering the third mixture obtained through agitation.

Examples of the proteolytic enzyme used in the operation of inputting pretreated porcine skin into an acid aqueous solution, in which proteolytic enzyme is dissolved, and mixing the mixture may include pepsin, bromelain, chymopapain, chymotrypsin, collagenase, ficin, papain, peptidase, proteolytic enzyme A, proteolytic enzyme K, trypsin, proteolytic enzyme of a microorganism, and a mixture thereof, but the disclosure is not limited thereto.

Although strong acid such as hydrochloric acid and weak acid such as acetic acid may be used as the acid solution used in the operation, preferably weak acid is used, and a mixing ratio of water and acid is 1%-20%, preferably 3%-10%. When the amount of acid is small, removing telopeptide is not smoothly performed, and when the amount is too much, not only telopeptide is removed, but also collagen is damaged.

In the preparing of the second mixture by inputting the first dough into the basic solution and agitating the mixture, and then adjusting pH, pH is 6-8 and may be adjusted by neutralizing with a weak base such as $Na_2CO_3$, $NaHCO_3$, and $Na_2HPO_4$.

In the preparing of the third mixture by inputting the second dough into the alcohol aqueous solution and agitating the mixture (S126), the alcohol may be methanol, ethanol, propanol, and isopropanol, as the solubility of collagen is affected by the mixing ratio of water and alcohol, the mixing ratio of water and alcohol is 5%-30%, preferably 10%-20%.

Thereafter, by the same method as the first embodiment, the bone grafting substitute having a hole is manufactured through the homogenization operation S130 and the collagen filtering operation S140.

Figure 9:
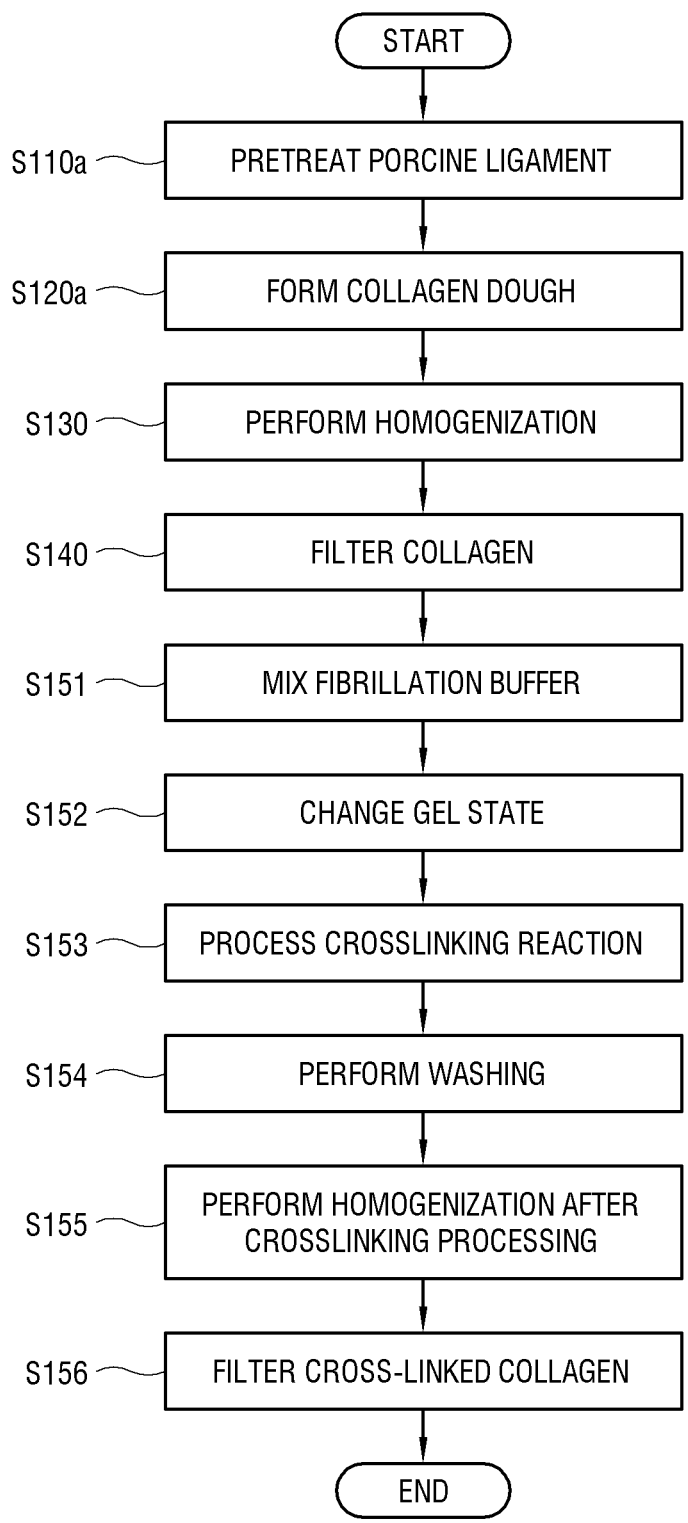
FIG. 9 is a flowchart showing, step by step, a collagen preparing operation of preparing cross-linked collagen, according to a first embodiment of the present inventive concept.

FIG. 9 is a flowchart showing, step by step, a collagen preparing operation of preparing cross-linked collagen, according to a first embodiment of the present inventive concept.

According to a method of manufacturing a bone grafting substitute having a hole a third embodiment of the present inventive concept, compared with the first and second embodiments, there is a difference in preparing cross-linked collagen in a collagen preparation operation S100c. However, there is no difference in the other operations of manufacturing a bone grafting substitute having a hole therebetween, the collagen preparation operation S100c is mainly described.

When cross-linked collagen having a cross-linked structure is used, a bone grafting substitute having a hole exhibiting excellent mechanical properties such as tensile strength and the like may be obtained.

The collagen preparation operation of preparing cross-linked collagen (S100c), as illustrated in detail in FIG. 9, after the collagen preparation operation S100a in the first embodiment of the present inventive concept, may further include a fibrillation buffer mixing operation (S151), a gel state change operation (S152), a crosslinking reaction processing operation (S153), a washing operation (S154), a homogenization operation after crosslinking processing (S155), and a cross-linked collagen filtering operation (S156).

However, the present inventive concept is not limited thereto, and may further include, after the collagen preparation operation S100b in the second embodiment of the present inventive concept, the fibrillation buffer mixing operation S151, the gel state change operation S152, the crosslinking reaction processing operation S153, the washing operation S154, the homogenization operation after crosslinking processing S155, and the cross-linked collagen filtering operation S156.

In other words, by processing crosslinking reaction after preparing any one collagen selected from among porcine ligament-derived collagen and porcine skin-derived collagen, cross-linked collagen may be obtained.

First, the fibrillation buffer mixing operation S151 is an operation of preparing a mixed solution by mixing the collagen obtained in the collagen filtering operation S140 with a fibrillation buffer having 20-30 parts by weight of sodium chloride, 1-3 parts by weight of sodium hydroxide, and 3-5 parts by weight of di-sodium hydrogen phosphate dihydrate with respect to 100 parts by weight of water.

Next, the gel state change operation S152 is an operation of preparing a mixture in a gel state by mixing the above mixed solution with γ-PGA and inputting the mixture into a well plate to change the mixture to be in a gel state in an incubator. In this state, a temperature of 4° C. or less and vacuum is maintained for 1-2 hours in a degassing state.

Next, the crosslinking reaction processing operation S153 is an operation of forming cross-linked collagen by mixing the gel-state mixture with a cross linking solution to have a crosslinking reaction.

Next, the washing operation S154 is an operation of washing out the cross linking solution mixed in the crosslinking reaction processing operation, and may include preparing a first mixture by tearing the cross-linked collagen into small pieces and inputting the pieces into a 15% ethanol aqueous solution (S154a), preparing a filtrate by agitating the first mixture and decompression-filtering the mixture (S154b), preparing a second mixture by tearing the filtrate into small pieces and inputting the pieces into the 15% ethanol aqueous solution (S154c), and agitating the second mixture and decompression-filtering the mixture (S154d).

The washing operation S154 may be repeated twice or more according to the washing result.

Next, the homogenization operation after crosslinking processing S155 is an operation of dissolving cross-linked collagen in a solvent to produce a homogenized cross-linked collagen solution, in which a 15% ethanol aqueous solution is input into a mixer, a filtrate filtered by the decompression-filtering of the washing operation S154 is torn into small pieces and input the solution, the mixture is agitated for 10 minutes in fast speed, and the mixed solution is homogenized by a homogenizer, thereby obtaining a homogenized cross-linked collagen solution.

Next, the cross-linked collagen filtering operation S156 is an operation of filtering cross-linked collagen from the homogenized cross-linked collagen solution, in which by removing supernatant liquid by centrifuging the homogenized cross-linked collagen solution obtained in the homogenization operation after crosslinking processing S155, thereby obtaining cross-linked collagen.

Thereafter, by mixing the cross-linked collagen obtained through centrifugation with a bone material, the bone grafting substitute having a hole is manufactured by the same method as that in the first and second embodiments.

While the present inventive concept has been described with respect to specific embodiments thereof, it will be apparent to those skilled in the art that various changes and modifications may be made without departing from the spirit and scope of the invention as defined in the following claims.

INDUSTRIAL APPLICABILITY

The present inventive concept may be used for a medical industry, particularly for a dental medical industry.

The invention claimed is:

1. A method of manufacturing a bone grafting substitute having a hole, the method comprising:
preparing biodegradable polymer;
preparing a molding material by mixing the biodegradable polymer with a bone material;
injecting the molding material into a hole forming mold for molding a bone grafting substitute having a hole; and
drying the molding material injected into the hole forming mold at a predetermined temperature,
wherein the biodegradable polymer is collagen, the collagen comprises porcine ligament-derived collagen, and preparing the collagen comprises:
pretreating porcine ligament to obtain collagen from the porcine ligament;
forming the pretreated porcine ligament into collagen dough;
mixing the collagen dough with an alcohol aqueous solution into a homogenized collagen solution; and
filtering collagen from the homogenized collagen solution.

2. The method of claim 1, wherein drying the molding material is by any one selected from among hot air drying and natural drying.

3. The method of claim 2, wherein a temperature for the hot air drying is 30°-150° C.

4. The method of claim 1, wherein the hole forming mold comprises:
an upper mold provided to mold the bone grafting substitute having a hole and comprising a plurality of bone grafting substitute main body holes that are formed by penetrating the upper mold and arranged apart from each other; and
a lower mold provided, when coupled to the upper mold, to allow the plurality of bone grafting substitute main body holes to form a shape of the bone grafting substitute having a hole, and
injecting the molding material comprises:
combining the upper mold to the lower mold; and
injecting the molding material into the hole forming mold in a state in which the upper mold and the lower mold are combined to each other.

5. The method of claim 4, wherein the lower mold comprises:
a base; and
a plurality of hole forming posts, each of the plurality of hole forming posts protruding upwards from the base, having a cross-sectional area less than a cross-sectional area of each of the plurality of bone grafting substitute main body holes, being arranged at a center area of each of the plurality of bone grafting substitute main body holes, and forming a center hole of the bone grafting substitute having a hole, and
in injecting the molding material, the molding material is injected into a space formed by the plurality of bone grafting substitute main body holes of the upper mold, the plurality of hole forming posts of the lower mold, and the base.

6. The method of claim 5, wherein the base and the plurality of hole forming posts are integrally provided.

7. The method of claim 5, wherein the lower mold further comprises a cut portion provided at one side of the base and having a predetermined cut region to facilitate separation of the upper mold from the lower mold in a state in which the upper mold and the lower mold are combined to each other, and
when drying the molding material is completed, the upper mold and the lower mold are separated from each other so that the bone grafting substitute having a hole is separated from the hole forming mold.

8. The method of claim 5, wherein a coupling post is provided on the base of the lower mold to be apart from the plurality of hole forming posts, and
a location fixing hole is provided in the upper mold at one side of the plurality of bone grafting substitute main body holes to fix a location of the upper mold on the lower mold through interference fit to the coupling post.

9. The method of claim 1, wherein the hole forming mold comprises:
an upper mold in which a plurality of bone grafting substitute main body holes are formed by penetrating the upper mold and arranged apart from each other, to mold the bone grafting substitute having a hole; and a lower mold comprising a plurality of hole forming posts, each of the plurality of hole forming posts having a cross-sectional area less than a cross-sectional area of each of the plurality of bone grafting substitute main body holes, arranged at a center area of each of the plurality of bone grafting substitute main body holes, and forming a center hole of the bone grafting substitute having a hole, and the upper mold and the lower mold are integrally provided.

10. The method of claim 1, wherein the bone grafting substitute having a hole has any one shape selected from among a circular ring shape and a polygonal block shape.

11. The method of claim 1, wherein, in preparing a molding material, the pH of the molding material is 4.0-9.0.

12. The method of claim 1, wherein a particle size of the bone material is 100 μm-2000 μm.

13. The method of claim 1, further comprising molding the molding material injected into the hole forming mold by freeze-drying at a temperature lower than room temperature.

14. The method of claim 1, wherein the pretreating porcine ligament comprises:
removing at least blood vessel and fat from the porcine ligament;
dipping the porcine ligament, from which the at least blood vessel and fat are removed, in an alcohol aqueous solution;
preparing cured porcine ligament by curing the porcine ligament at a temperature lower than a predetermined reference temperature; and
cutting the cured porcine ligament into a predetermined size.

15. The method of claim 1, wherein the forming the pretreated porcine ligament into collagen dough comprises:
inputting the pretreated porcine ligament into an acid aqueous solution, in which proteolytic enzyme is dissolved, and mixing a mixture using a Stephan mixer;
preparing a first mixture by adding an acid aqueous solution to a mixed solution and agitating a mixture;
preparing a first dough by removing liquid from the first mixture obtained through agitation;
preparing a second mixture by inputting the first dough into a basic solution and agitating a mixture, and adjusting pH;
preparing a second dough by removing liquid from the second mixture obtained through agitation;
preparing a third mixture by inputting the second dough into an alcohol aqueous solution and agitating a mixture; and
forming collagen dough by removing liquid from the third mixture obtained through agitation.

16. The method of claim 1, wherein filtering collagen comprises:
centrifuging the homogenized collagen solution; and
obtaining collagen by removing supernatant liquid generated after centrifugation.

17. The method of claim 1, wherein the collagen comprises cross-linked collagen that is cross-linked to have a cross-linked structure,
the method further comprising, after filtering collagen:
preparing a mixed solution by mixing the collagen obtained in filtering collagen with a fibrillation buffer having 20-30 parts by weight of sodium chloride, 1-3 parts by weight of sodium hydroxide, and 3-5 parts by weight of di-sodium hydrogen phosphate dihydrate with respect to 100 parts by weight of water;
preparing a gel state mixture by mixing the mixed solution with γ-PGA and inputting a mixture into a well plate to change the mixture to be in a gel state in an incubator;
mixing the gel-state mixture with a cross linking solution to have a crosslinking reaction;
washing out the cross linking solution mixed in the crosslinking reaction processing operation;
dissolving the cross-linked collagen in a solvent to produce a homogenized cross-linked collagen solution; and
filtering the cross-linked collagen from the homogenized cross-linked collagen solution.

18. The method of claim 17, wherein the washing out comprises:
preparing a first mixture by tearing the cross-linked collagen into small pieces and inputting the pieces into an alcohol aqueous solution;
preparing a filtrate by agitating the first mixture and decompression-filtering a mixture; preparing a second mixture by tearing the filtrate into small pieces and inputting the pieces into an alcohol aqueous solution; and
agitating the second mixture and decompression-filtering a mixture.

19. The method of claim 1, wherein the biodegradable polymer is collagen, the collagen comprises porcine skin-derived collagen, and the collagen preparation operation comprises:
a porcine skin pretreatment operation of pretreating porcine skin to obtain collagen from the porcine skin;
a collagen dough forming operation of forming the pretreated porcine skin into collagen dough;
a homogenization operation of mixing the pretreated porcine skin with an alcohol aqueous solution into a homogenized collagen solution; and
a collagen filtering operation of filtering collagen from the homogenized collagen solution.

20. The method of claim 19, wherein the porcine skin pretreatment operation comprises:
cutting frozen porcine skin into a predetermined size;
removing fat by inputting cut porcine skin into an organic solvent and agitating a mixture; and
removing the organic solvent by washing out porcine skin, from which fat is removed, with distilled water.

21. The method of claim 1, wherein the biodegradable polymer comprises any one biodegradable polymer selected from among fibrinogen, chitosan, gelatin, cellulose, hyaluronic acid, dextran, and cross-linked fibrinogen, cross-linked chitosan, cross-linked gelatin, cross-linked cellulose, cross-linked hyaluronic acid, and cross-linked dextran, which are cross-linked to have a cross-linked structure.

22. The method of claim 1, wherein the bone material comprises any one heterogeneous bone selected from among bovine bones, horse bones, and porcine bones.

23. The method of claim 1, wherein the bone material comprises any one selected from among artificially synthesized bone, bioceramic-based bone containing calcium phosphate and natural ceramic or coral.

24. The method of claim 1, wherein, in the bone grafting substitute having a hole, a thickness of a bone grafting substitute main body surrounding the hole is 1.5 mm-5 mm.

25. The method of claim 24, wherein the bone grafting substitute having a hole has a hole having a diameter of 2 mm-8 mm and a height of 2 mm-10 mm.

\* \* \* \* \*